United States Patent
Kovi et al.

(10) Patent No.: US 12,396,999 B2
(45) Date of Patent: Aug. 26, 2025

(54) COMPOSITION OF FERRIC MALTOL FOR ORAL ADMINISTRATION

(71) Applicant: RK PHARMA INC., Pearl River, NY (US)

(72) Inventors: Ravishanker Kovi, North Brunswick, NJ (US); Prasad Vure, Vadodara (IN); Raghu Rami Reddy Kasu, Pearl River, NY (US); Thupalli Ajey Kumar Reddy, Bangalore (IN); Yekkanti Vamshi, Bangalore (IN); Jayraman Kannappan, Vadodara (IN); Hardik Vyas, Vadodara (IN)

(73) Assignee: RK PHARMA INC., Pearl River, NY (US)

( * ) Notice: Subject to any disclaimer, the term of this patent is extended or adjusted under 35 U.S.C. 154(b) by 0 days.

(21) Appl. No.: 17/874,838

(22) Filed: Jul. 27, 2022

(65) Prior Publication Data

US 2023/0054302 A1 Feb. 23, 2023

Related U.S. Application Data

(60) Provisional application No. 63/230,109, filed on Aug. 6, 2021.

(51) Int. Cl.
*A61K 31/555* (2006.01)
*A61K 9/48* (2006.01)

(52) U.S. Cl.
CPC ............ *A61K 31/555* (2013.01); *A61K 9/485* (2013.01); *A61K 9/4858* (2013.01); *A61K 9/4866* (2013.01)

(58) Field of Classification Search
CPC .... A61K 31/555; A61K 9/485; A61K 9/4858; A61K 9/4866
See application file for complete search history.

(56) References Cited

U.S. PATENT DOCUMENTS

2017/0304314 A1* 10/2017 Mallard .................... A61P 7/06

OTHER PUBLICATIONS

European Medicines Agency, titled "Committee for Medicinal Products for Human Use. Assessment Report on Feraccru." (Dec. 17, 2015) (Year: 2015).*
Federal Drug Administration-Center for Drug Evaluation and Research, titled "Accrufer (ferric maltol) Capsules-Product Quality Reviews." (Sep. 27, 2018) (Year: 2018).*

* cited by examiner

*Primary Examiner* — Clinton A Brooks
*Assistant Examiner* — Josmalen M. Ramos-Lewis
(74) *Attorney, Agent, or Firm* — Nikitas E. Nicolakis

(57) ABSTRACT

The invention relates to an improved composition of ferric maltol or ferric trimaltol for the treatment of iron deficiency, wherein the composition comprises the active ferric maltol or ferric trimaltol lower than 60% of the total composition weight. The compositions further can be a capsule or tablet or any other pharmaceutical solid dosage form, preferably a capsule in a hard gelatin in a size of 0 or 1, for oral administration.

2 Claims, No Drawings

COMPOSITION OF FERRIC MALTOL FOR ORAL ADMINISTRATION

FIELD OF THE INVENTION

The present invention provides an improved oral composition of ferric maltol or ferric trimaltol in the form of solid oral pharmaceutical dosage form comprising the active ferric maltol in the concentration lower than 60% of the total composition weight of the formulation.

BACKGROUND OF THE INVENTION

Chemically, Ferric maltol contains iron in a stable ferric state as a complex with a trimaltol ligand. Ferric maltol is 3-hydroxy-2-methyl-4H-pyrane-4-one iron (III) complex (3:1) and has the molecular formula (C6H5O3)3Fe and a molecular mass of 431.2; having the following formula:

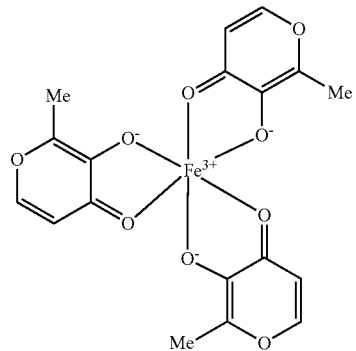

The molar ratio of iron to hydroxy pyrone is 1:3

Marketed Accrufer® is a red capsule, printed with "30", containing colloidal anhydrous silica, crospovidone (Type A), lactose monohydrate, magnesium stearate and sodium lauryl sulfate as inactive ingredients. In addition, the capsule shell contains FD&C Blue No. 1, FD&C Red No. 40, FD&C Yellow No.6, hypromellose and titanium dioxide. The ink used for printing the marking contains ammonium hydroxide, ethanol, iron oxide black and propylene glycol.

ACCRUFER (ferric maltol) capsules, an iron replacement product for oral administration, contain 30 mg iron and 201.5 mg maltol. Iron deficiency anaemia is characterized by low levels of iron in the blood which can be due to nutritional deficiency that is insufficient dietary intake of iron, or loss of iron from serious internal bleeding caused by diseases of the gastrointestinal or urinary tract, for example inflammatory bowel diseases such as Crohn's disease and ulcerative colitis.

U.S. Pat. No. 45,75,502 discloses pharmaceutical compositions containing an iron complex of a 3-hydroxy-4-pyrone. The iron is in a ferric state.

PCT application WO 1996, 041627 discloses composition of iron complexes with hydroxypyrone with different molar ratios and with acid salts for providing iron in cases of anaemia. Our disclosed invention is different from the PCT '627 wherein pharmaceutical composition is an improved solid composition of ferric maltol or ferric trimaltol for oral administration.

PCT application WO 2002,024196 discloses composition of ferrous salts and hydroxypyrone for increasing iron level in a patient's bloodstream. Our disclosed invention differs from the PCT '196 in a way directed towards an improved composition of ferric maltol for oral administration.

US 2021/0139518 A discloses crystalline Ferric maltol alfa form and also processes for the preparation of highly pure crystalline alfa form. Our disclosed invention provides improved pharmaceutical compositions of ferric maltol in the form of alpha form for oral administration, wherein the ferric maltol in the composition below 60% of the combined composition weight in solid oral dosage form.

U.S. Pat. No. 10,179,120 patent discloses method of treating iron deficiency by oral administration of ferric maltol, specifically claiming the percentage of ferric trimaltol is at least 60% of the combined weight of ferric trimaltol and excipients, as a 30 mg elemental iron in size 1 capsule. Our disclosed invention differs from U.S. Pat. No. '120 in a way directed towards an improved composition of ferric maltol for oral administration wherein the concentration of ferric maltol is at lower than 60% of the combined weight of ferric trimaltol and excipients.

An object of the present invention is to provide an improved solid oral composition of ferric maltol, a concentration of ferric maltol below 60% of the combined composition weight in solid oral dosage form.

The currently marketed form of ferric maltol has at least 60% of ferric maltol, of the combined with of active ingredient and excipients. The inventors have surprisingly found an improved composition of ferric maltol or ferric trimaltol in the form a tablet and a capsule for oral administration twice daily, wherein the composition comprises the active ferric maltol lower than 60% of the total composition weight.

SUMMARY OF THE INVENTION

An embodiment of the present invention provides the preparation comprising 231.5 mg of ferric maltol or ferric trimaltol and one or more other excipients wherein said ferric maltol or ferric trimaltol formulation comprises lower than 60% of ferric maltol or ferric trimaltol.

Another embodiment of the present invention provides preparation comprising 231.5 mg of ferric maltol or ferric trimaltol and one or more other excipients wherein said ferric maltol or ferric trimaltol formulation comprises lower than 58% of ferric maltol or ferric trimaltol.

Another embodiment of the present invention provides preparation comprising 231.5 mg of ferric maltol or ferric trimaltol and one or more other excipients wherein said ferric maltol or ferric trimaltol formulation comprises lower than 55% of ferric maltol or ferric trimaltol.

An embodiment of the present invention provides preparation comprising 231.5 mg of ferric maltol or ferric trimaltol, wherein said ferric maltol or ferric trimaltol formulation comprises lower than 60% of ferric maltol or ferric trimaltol in the form of capsule or tablet for oral administration.

An embodiment of the present invention provides preparation comprising 231.5 mg of ferric maltol or ferric trimaltol, wherein said ferric maltol or ferric trimaltol formulation comprises lower than 60% of ferric maltol or ferric trimaltol in the form of capsule or tablet for oral administration, wherein the composition is manufactured either by dry granulation or wet granulation or direct compression or direct filling of granules or combinations thereof.

An embodiment of the present invention provides preparation comprising 231.5 mg of ferric maltol or ferric trimaltol, wherein said ferric maltol or ferric trimaltol formulation comprises lower than 60% of ferric maltol or ferric trimaltol in the form of capsule or tablet for oral administration, wherein the composition is manufactured and filled into hard gelatin capsules of size 0 or 1 and preferably size 1

In another embodiment of present invention provides, the formulations having a dissolution profile of more than 90% drug release in pH 1.2, preferably more than 95% drug release, wherein it is comparable with marketed preparation.

In another embodiment of the present invention, ferric maltol or ferric trimaltol is in the alpha crystalline form.

In another embodiment the present invention provides composition using novel polymorphic forms RK1, RK2, RK3, RK4, RK5, RK6 and RK7 of Ferric maltol.

In an another embodiment of present invention provides ferric maltol or ferric trimaltol is in the form of alpha crystalline form, novel polymorphic forms RK1, RK2, RK3, RK4, RK5, RK6 and RK7 of ferric maltol, wherein said ferric maltol or ferric trimaltol formulation comprises lower than 60% of ferric maltol or ferric trimaltol in the form of capsule or tablet for oral administration, preferably lower than 58%, more preferably lower than 55%

The details of one or more embodiments of the invention are set forth in the description below. Other features, examples, objects and advantages of the invention will be apparent from the description.

DETAILED DESCRIPTION OF THE PREFERRED EMBODIMENTS

The present invention now will be described more fully hereinafter with reference to the accompanying examples and experiments, in which illustrative embodiments of the invention are mentioned. The examples provided herein are exemplary and not limiting the scope of the invention; and any modification or variation can be apparent to any person skilled in the art related to the invention. This invention may, however, be embodied in many different forms and should not be construed as limited to the embodiments set forth herein; rather, these embodiments and examples are provided so that this disclosure will be thorough and complete, and will fully convey the scope of the invention to those skilled in the art.

The terminology used herein is for the purpose of describing particular embodiments only and is not intended to be limiting the scope of the invention. As used herein, the singular forms "a", "an" and "the" are intended to include the plural forms as well, unless the context clearly indicates otherwise. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "Ferric maltol" refers to Ferric (III) and its complex with maltol to increase the bioavailability of iron.

As used herein, the term "dosage form" refers to, unless otherwise specified, oral pharmaceutical composition in the form of powders, tablets, capsules, mini-tablets, granules, pellets, troches, pellets, beads, particulates.

As used herein, the term "oral" refers to, route of administration of the disclosed invention which is either swallowed or that may be mixed or taken with food, unless otherwise particularly specified.

As used herein, and unless otherwise specified, the term "storage-stable" refers to physical and chemical stability of the solid oral formulation disclosed in the invention.

The pharmaceutical compositions of the present invention may be adapted for oral administration. The formulations disclosed provide a free-flowing powder composition that can be formulated into tablets, mini-tablets, granules, pellets, troches and other dosage forms. Powder forms of the pharmaceutical composition, such as tablets, mini-tablets, granules, sprinkles, pellets, beads, particles, particulates, troches and other dosage forms containing powder forms of the pharmaceutical composition can be contained in capsules, pouches, packets, sachets, bottles or blister packs. Tablets, mini-tablets, granules, sprinkles, pellets, beads, particulates, or particles or other granulated forms can also be compressed into other solid oral dosage forms.

Conveniently, the formulation is the form of powder wherein, the active ingredient and pharmaceutical excipients can be in the form of anhydrous or crystalline form.

In at least one aspect, a crystalline Ferric maltol form alfa is provided that is characterized by a PXRD pattern having peaks at 9.4, 12.7, 14.4, 15.2, 17.3, 19.8, 21.1, 23, 24.3° 2θ±0.2° 2θ

In a preferred embodiment of the invention, polymorphic form RK1 can be characterized by XRPD comprising characteristic peaks at 5.4, 11.5, 12.5, 16.0, 16.4, 23.4 and 24.2±0.2° 2θ

In a preferred embodiment of the invention, polymorphic form RK2 can be characterized by XRPD comprising characteristic peaks at 6.8, 10.6, 12.2, 13.83, 15.23, 15.84, 22.9, 24.2±0.2° 2θ.

In a preferred embodiment of the invention, polymorphic form RK3 which is a Dichloromethane solvate of Ferric maltol can be characterized by XRPD comprising characteristic peaks at 11.5, 14.2, 18.3, 23.3, 24.9±0.2° 2θ.

In a preferred embodiment of the invention, polymorphic form RK4 which is a Chlorobenzene solvate of Ferric maltol can be characterized by XRPD comprising characteristic peaks at 7.5, 9.1, 11.9, 13.6, 17.1, 22.0 and 22.7±0.2° 2θ.

In a preferred embodiment of the invention, polymorphic form RK5 which is a Carbon tetrachloride Solvate of Ferric maltol can be characterized by XRPD comprising characteristic peaks at 9.6, 14.5, 16.3, 19.3, 22.0 and 22.2±0.2° 2θ.

In a preferred embodiment of the invention, polymorphic form RK6 which is a Acetic acid hemi solvate of Ferric maltol can be characterized by XRPD comprising characteristic peak at 6.6±0.2° 2θ, and two or more further peaks at 11.6, 13.3, 16.4 and 23.9±0.2° 2θ.

In a preferred embodiment of the invention, polymorphic form RK7 which is an Acetic acid hemi solvate of Ferric maltol can be characterized by XRPD comprising characteristic peaks at 5.1, 6.0, 10.3, 13.0, 15.0, 18.0, and 23.8±0.2° 2θ.

In at least one aspect, a pharmaceutical composition is provided that includes a highly pure crystalline alpha form of Ferric maltol and one or more pharmaceutically acceptable excipients in the form of a solid oral dosage form.

In at least one aspect, a pharmaceutical composition is provided that includes a highly pure polymorphic form from RK1, RK2, RK3, RK4, RK5, RK6, RK7 of Ferric maltol and one or more pharmaceutically acceptable excipients in the form of a solid oral dosage form.

The oral solid formulation can be in the form of immediate release, extended release, controlled release, modified release, pulsatile release, dual release pharmaceutical compositions.

Ferric maltol may be combined with an oral, non-toxic, inert carrier or diluent such as not limited to lactose, gelatin, agar, starch, sucrose, glucose, dicalcium phosphate, calcium sulphate, mannitol, sorbitol and microcrystalline cellulose and its derivatives. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol and waxes. Dissolution enhancing agents or wetting agents that are anionic, cationic or non-ionic in nature like alkyl sulphate salts, sodium lauryl sulphate, without limitation. Lubricants used in these dosage forms may include sodium oleate, sodium stearate, sodium benzoate, sodium acetate, sodium chloride, stearic acid, sodium stearyl fumarate, and talc. Disintegrants include, without limitation, starch, methyl cellulose, agar, bentonite, xanthan gum, croscarmellose sodium, and sodium starch glycolate.

As used herein, and unless otherwise specified, the term "about" means an acceptable error for a particular value as determined by one of ordinary skill in the art, which depends in part on how the value is measured or determined. In certain embodiments, the term about means within 10%, 9%, 8%, 7%, 6%, 5%, 4%, 3%, 2%, 1%, 0.5%, 0.1%, or 0.05% of a given value or range.

The solid oral dosage form comprising about 25 mg to 30 mg of iron, more preferably about 30 mg of elemental iron in the form of iron (III) form.

In one embodiment, a 30 mg of the iron preparation and the preparation comprising 231.5 mg of ferric maltol or ferric trimaltol and one or more other excipients wherein said ferric maltol or ferric trimaltol formulation comprises lower than 60% of ferric maltol or ferric trimaltol of the combined weight with excipients.

In one embodiment, a 30 mg of the iron preparation and the preparation comprising 231.5 mg of ferric maltol or ferric trimaltol and one or more other excipients wherein said ferric maltol or ferric trimaltol formulation comprises lower than 58% of ferric maltol or ferric trimaltol.

In one embodiment, a 30 mg of the iron preparation and the preparation comprising 231.5 mg of ferric maltol or ferric trimaltol and one or more other excipients wherein said ferric maltol or ferric trimaltol formulation comprises lower than 55% of ferric maltol or ferric trimaltol.

In another embodiment, the formulation is in the form of a unit capsule. The present invention utilizes hard gelatin capsule dosage form for the administration of ferric maltol wherein capsule sizes can be 000, 00, 0, 1, 2, 3, 4, 5

In one of the other embodiments of the present invention is directed towards formulation of hard gelatin capsule dosage form of size 0 or 1

Pharmaceutically acceptable additional excipients or adjuvants optionally include but are not limited to one or more preservatives, polymers, buffers, surfactants, chelating agents, drug release modifying agents, binding agents, tonicity modifying agents and antioxidants.

Formulations in accordance with the present disclosure have performed dissolution studies using USP type II (Paddle with sinker) rotated at 75 r.p.m. and dissolution medium used is tier I KCl/HCl buffer of pH 1.2 with or without pepsin. The volume of the dissolution medium is 1000 ml, further sampling times in minutes are at 5, 10, 15, 20, 30 and 45.

Formulations in accordance with the present disclosure have a dissolution profile of more than 90% drug release in pH 1.2, more preferably more than 95% drug release.

Formulation in accordance with the present disclosure comprises diluents, not limited to lactose monohydrate, mannitol, in the concentration range of about 30-55% w/w, more preferably in the concentration range of about 35-45% w/w.

Formulation in accordance with the present disclosure comprises wetting agents or surfactants, not limited to sodium lauryl sulphate, in the concentration range of about 0.5-1.5% w/w, more preferably in the concentration range of about 0.75-1.0% w/w.

Formulation in accordance with the present disclosure comprises disintegrants, not limited to crospovidone, in the concentration range of about 2.0-5.0% w/w, more preferably in the concentration range of 2.0-3.0% w/w.

Formulation in accordance with the present disclosure comprises glidants, not limited to colloidal silicon dioxide, in the concentration range of about 0.1-1% w/w, more preferably in the concentration range of 0.1-0.5% w/w.

Formulation in accordance with the present disclosure comprises lubricants, not limited to magnesium stearate, in the concentration range of about 0.1-2.0% w/w, more preferably in the concentration range of 0.1-1.0% w/w.

Formulation in accordance with the present disclosure has a fill weight of about 400-600 mg including the active ingredient ferric maltol and pharmaceutically acceptable excipients, wherein said ferric maltol or ferric trimaltol formulation comprises lower than 60% of ferric maltol or ferric trimaltol of the total combined weight.

Certain specific aspects and embodiments of the present application will be explained in more detail with reference to the following examples, without wishing to be bound by a theory, which are provided only for purposes of illustration and should not be construed as limiting the scope of the present application in any manner.

While the foregoing pages provide a detailed description of the preferred embodiments of the invention, it is to be understood that the summary, description and examples are illustrative only of the core of the invention and non-limiting. Furthermore, as many changes can be made to the invention without departing from the scope of the invention, it is intended that all material contained herein may be interpreted as mere illustrative of the invention and not in a limiting sense.

EXAMPLES

The following examples are for the illustration only and are not intended in any way to limit the scope of the present invention.

Example 1

TABLE 1

| Sr. No | Name of the Ingredient with Pharmacopeial status | FMLC/169/001/01 | |
|---|---|---|---|
| | | Mg/Capsule | % w/w |
| 1. | Ferric Maltol - IH | 231.50 | 57.87 |
| 2. | Lactose Monohydrate, USP/NF | 152.90 | 38.22 |
| 3. | Sodium lauryl sulphate, USP/NF | 3.00 | 0.75 |
| 4. | Crospovidone, USP/NF | 9.00 | 2.25 |
| 5. | Colloidal silicon dioxide, NF | 0.60 | 0.15 |
| 6. | Magnesium Stearate, NF | 3.00 | 0.75 |
| | Total | 400.00 | 100.00 |

Preparation:
Preparation requires dry blending followed by capsule filling. Ferric Maltol and Lactose monohydrate were sifted through a suitable sieve and transferred into a blender. Sodium lauryl sulphate, Crospovidone and colloidal silicone dioxide were sifted through suitable sieve and transferred into a blender and mixed for 15 minutes. Blend was compacted using a suitable compactor, passed through a suitable sieve and mixed for 5 min in the blender. Magnesium stearate was sifted through a suitable sieve. The above sifted magnesium stearate was added to the blender and mixed for 5 minutes. Above blend was filled in size 1 Capsule.

| Weight of capsule shell | 75.00 mg |
|---|---|
| Fill Weight | 400.00 mg |
| Final Weight | 475.00 mg |

Dissolution testing is summarized in Table 1A

TABLE 1A

| Dissolution testing | |
|---|---|
| Dissolution Media | KCl/HCl Buffer, pH 1.2 |
| RPM | 75.00 |
| Apparatus | Type II Paddle |
| Volume | 1000 mL |
| Time Points (Minutes) | 5, 10, 15, 20, 30 and 45 minutes |
| % Drug Dissolved | |
| 5 Minutes | 96 |
| 10 Minutes | 96.3 |
| 15 Minutes | 96.4 |
| 20 Minutes | 96.7 |
| 30 Minutes | 97 |
| 45 Minutes | 97 |

Example 2

TABLE 2

| Sr. No | Name of the Ingredient with Pharmacopeial status | FMLC/169/001/03 | |
|---|---|---|---|
| | | Mg/Capsule | % w/w |
| 1. | Ferric Maltol - IH | 231.50 | 51.44 |
| 2. | Lactose Monohydrate, USP/NF | 202.90 | 45.08 |
| 3. | Sodium lauryl sulphate, USP/NF | 3.00 | 0.75 |
| 4. | Crospovidone, USP/NF | 9.00 | 2.25 |
| 5. | Colloidal silicon dioxide, NF | 0.60 | 0.15 |
| 6. | Magnesium Stearate, NF | 3.00 | 0.75 |
| | Total | 450.00 | 100.00 |

Preparation:

Required quantities of Ferric Maltol and Lactose monohydrate were sifted through suitable sieve and transferred into a blender. Sodium lauryl sulphate, Crospovidone and colloidal silicone dioxide were sifted through suitable sieve and transferred into a blender and mixed for 15 minutes. Blend was compacted using a suitable compactor, passed through a suitable sieve and mixed for 5 min in the blender. Magnesium stearate was sifted through a suitable sieve. The above sifted magnesium stearate was added to the blender and mixed for 5 minutes. Above blend was filled in size 0/1 Capsule.

| Weight of capsule shell | 75.00 mg |
|---|---|
| Filled weight | 450.00 mg |
| Final weight | 525.00 mg |

Dissolution Testing is Summarized in Table 2A

| Dissolution Media | KCl/HCl Buffer, pH 1.2 |
|---|---|
| RPM | 75.00 |
| Apparatus | Type II Paddle |
| Volume | 1000 mL |
| Time Points (Minutes) | 5, 10, 15, 20, 30 and 45 minutes |
| % Drug Dissolved | |
| 5 Minutes | 92.2 |
| 10 Minutes | 92.4 |
| 15 Minutes | 92.7 |
| 20 Minutes | 92.8 |
| 30 Minutes | 93 |
| 45 Minutes | 93 |

Example 3

TABLE 3

| Sr. No | Name of the Ingredient with Pharmacopeial status | FMLC/169/001/05 | |
|---|---|---|---|
| | | Mg/Capsule | % w/w |
| 1. | Ferric Maltol - IH | 231.50 | 57.87 |
| 2. | Mannitol USP/NF | 152.90 | 38.22 |
| 3. | Sodium lauryl sulphate USP/NF | 3.00 | 0.75 |
| 4. | Crospovidone USP/NF | 9.00 | 2.25 |
| 5. | Colloidal silicon dioxide NF | 0.60 | 0.15 |
| 6. | Magnesium Stearate NF | 3.00 | 0.75 |
| | Total | 400.00 | 100.00 |

Preparation:

Required quantities of Ferric Maltol and Lactose monohydrate were sifted through suitable sieve and transferred into a blender. Sodium lauryl sulphate, Crospovidone and colloidal silicone dioxide were sifted through suitable sieve and transferred into a blender and mixed for 15 minutes. Blend was compacted using a suitable compactor, passed through a suitable sieve and mixed for 5 min in the blender. Magnesium stearate was sifted through a suitable sieve. The above sifted magnesium stearate was added to the blender and mixed for 5 minutes. Above blend was filled in size 0/1 Capsule.

| Weight of capsule shell | 75.00 mg |
|---|---|
| Filled weight | 400.00 mg |
| Final weight | 475.00 mg |

Dissolution Testing is Summarized in Table 3A

| Dissolution Media | KCl/HCl Buffer, pH 1.2 |
|---|---|
| RPM | 75.00 |
| Apparatus | Type II Paddle |
| Volume | 1000 mL |
| Time Points (Minutes) | 5, 10, 15, 20, 30 and 45 minutes |

-continued

| % Drug Dissolved | |
|---|---|
| 5 Minutes | 96.3 |
| 10 Minutes | 96.4 |
| 15 Minutes | 96.6 |
| 20 Minutes | 96.9 |
| 30 Minutes | 97 |
| 45 Minutes | 97 |

Example 4

TABLE 4

| | | FMLC/169/001/05 | |
|---|---|---|---|
| Sr. No | Name of the Ingredient with Pharmacopeial status | Mg/ Capsule | % w/w |
| 1. | Ferric Maltol - IH (polymorphic forms- RK1, RK2, RK3, RK4) | 231.50 | 57.87 |
| 2. | Mannitol USP/NF | 152.90 | 38.22 |
| 3. | Sodium lauryl sulphate USP/NF | 3.00 | 0.75 |
| 4. | Crospovidone USP/NF | 9.00 | 2.25 |
| 5. | Colloidal silicon dioxide NF | 0.60 | 0.15 |
| 6. | Magnesium Stearate NF | 3.00 | 0.75 |
| | Total | 400.00 | 100.00 |

Preparation:

Required quantity of Ferric Maltol of RK1, RK2, RK3 & RK4 polymorphic forms separately and Lactose monohydrate were sifted through suitable sieve and transferred into blender. Sodium lauryl sulphate, Crospovidone and colloidal silicone dioxide were sifted through suitable sieve and transferred into a blender and mixed for 15 minutes. Blend was compacted using a suitable compactor, passed through a suitable sieve and mixed for 5 min in the blender. Magnesium stearate was sifted through a suitable sieve. The above sifted magnesium stearate was added to the blender and mixed for 5 minutes. Above blend was filled in size 0/1 Capsule.

| Weight of capsule shell | 75.00 mg |
|---|---|
| Filled weight | 400.00 mg |
| Final weight | 475.00 mg |

Dissolution Testing is Summarized in Table 4A

| Dissolution Media | KCl/HCl Buffer, pH 1.2 |
|---|---|
| RPM | 75.00 |
| Apparatus | Type II Paddle |
| Volume | 1000 mL |
| Time Points (Minutes) | 5, 10, 15, 20, 30 and 45 minutes |
| % Drug Dissolved | |
| 5 Minutes | 96.5 |
| 10 Minutes | 96.6 |
| 15 Minutes | 96.8 |
| 20 Minutes | 96.8 |
| 30 Minutes | 96.9 |
| 45 Minutes | 97 |

Example 5

TABLE 5

| | | FMLC/169/001/05 | |
|---|---|---|---|
| Sr. No | Name of the Ingredient with Pharmacopeial status | Mg/ Capsule | % w/w |
| 1. | Ferric Maltol - IH (polymorphic forms- RK5, RK6, RK7) | 231.50 | 51.44 |
| 2. | Mannitol USP/NF | 202.90 | 45.08 |
| 3. | Sodium lauryl sulphate USP/NF | 3.00 | 0.75 |
| 4. | Crospovidone USP/NF | 9.00 | 2.25 |
| 5. | Colloidal silicon dioxide NF | 0.60 | 0.15 |
| 6. | Magnesium Stearate NF | 3.00 | 0.75 |
| | Total | 450.00 | 100.00 |

Preparation:

Required quantity of Ferric Maltol of RK5, RK6, & RK7 polymorphic forms separately and Lactose monohydrate were sifted through suitable sieve and transferred into blender. Sodium lauryl sulphate, Crospovidone and colloidal silicone dioxide were sifted through suitable sieve and transferred into a blender and mixed for 15 minutes. Blend was compacted using a suitable compactor, passed through a suitable sieve and mixed for 5 min in the blender. Magnesium stearate was sifted through a suitable sieve. The above sifted magnesium stearate was added to the blender and mixed for 5 minutes. Above blend was filled in size 0/1 Capsule.

| Weight of capsule shell | 75.00 mg |
|---|---|
| Filled weight | 450.00 mg |
| Final weight | 525.00 mg |

Dissolution Testing is Summarized in Table 5A

| Dissolution Media | KCl/HCl Buffer, pH 1.2 |
|---|---|
| RPM | 75.00 |
| Apparatus | Type II Paddle |
| Volume | 1000 mL |
| Time Points (Minutes) | 5, 10, 15, 20, 30 and 45 minutes |
| % Drug Dissolved | |
| 5 Minutes | 96.1 |
| 10 Minutes | 96.2 |
| 15 Minutes | 96.5 |
| 20 Minutes | 97 |
| 30 Minutes | 97.2 |
| 45 Minutes | 97.5 |

The composition described in the examples 1-5 were also manufactured using the dry granulation and the granules were filled directly or further processed for slugging based on the requirement of the bulk weight/density of the filled material into the required capsule.

The invention claimed is:

1. A capsule dosage form consisting of: ferric maltol or ferric trimaltol as active ingredient and pharmaceutically acceptable excipients, wherein ferric maltol or ferric trimaltol is acetic acid solvate form in a formulation consisting of lower than 55% of ferric maltol or ferric trimaltol of the combined weight with excipients and with a total impurity lower than 1%, and with a 1-(2-furyl) ethanol lower than 0.5% at 40° C./75% RH.

2. The formulation of claim 1, wherein the ferric maltol or ferric trimaltol formulation has a concentration equivalent to 25 to 35 mg of elemental iron.

\* \* \* \* \*